(12) United States Patent
Hudson et al.

(10) Patent No.: US 7,018,392 B2
(45) Date of Patent: Mar. 28, 2006

(54) HEMOSTATIC SYSTEM FOR BODY CAVITIES

(75) Inventors: John Overton Hudson, Leicester (GB); Alberto Bauer, Marella/Malaga (ES)

(73) Assignee: Arthrocare Corporation, Austin, TX (US)

( * ) Notice: Subject to any disclaimer, the term of this patent is extended or adjusted under 35 U.S.C. 154(b) by 281 days.

(21) Appl. No.: 09/998,524

(22) Filed: Nov. 28, 2001

(65) Prior Publication Data

US 2002/0077653 A1 Jun. 20, 2002

Related U.S. Application Data

(63) Continuation-in-part of application No. 09/927,864, filed on Aug. 10, 2001, now Pat. No. 6,706,051, which is a continuation-in-part of application No. 09/406,166, filed on Sep. 27, 1999, now Pat. No. 6,306,154, which is a continuation-in-part of application No. 09/057,414, filed on Apr. 8, 1998, now abandoned.

(51) Int. Cl.
*A61M 29/00* (2006.01)

(52) U.S. Cl. .................................. 606/192; 606/191
(58) Field of Classification Search ................ 606/213, 606/151; 604/11
See application file for complete search history.

(56) References Cited

U.S. PATENT DOCUMENTS

| | | | |
|---|---|---|---|
| 2,493,326 A | 1/1950 | Trinder | |
| 2,847,997 A | 8/1958 | Tibone | |
| 3,049,125 A | 8/1962 | Kriwkowitsch | |
| 3,420,237 A | 1/1969 | Fortay | |
| 3,483,859 A * | 12/1969 | Pittman | 600/371 |
| 3,516,407 A | 6/1970 | Ruggero | |
| 3,618,607 A * | 11/1971 | Ells et al. | 604/368 |
| 3,766,924 A | 10/1973 | Pidgeon | |
| 4,041,948 A * | 8/1977 | Flam et al. | 604/369 |
| 4,338,941 A | 7/1982 | Payton | |
| 4,364,392 A | 12/1982 | Strother et al. | |
| 4,619,261 A | 10/1986 | Guerriero | |
| 4,638,803 A | 1/1987 | Rand | |
| 4,686,962 A | 8/1987 | Haber | |
| 4,832,680 A | 5/1989 | Haber et al. | |
| 4,883,465 A | 11/1989 | Brennan | |
| 5,061,274 A | 10/1991 | Kensey | |
| 5,100,385 A | 3/1992 | Bromander | |
| 5,176,692 A | 1/1993 | Wilk et al. | |
| 5,224,497 A | 7/1993 | Ehlers | |
| 5,263,966 A * | 11/1993 | Daneshvar | 606/201 |
| 5,308,326 A | 5/1994 | Zimmon | |
| 5,312,435 A | 5/1994 | Nash et al. | |
| 5,376,067 A * | 12/1994 | Daneshvar | 602/58 |

(Continued)

FOREIGN PATENT DOCUMENTS

EP 0 252 607 5/1987

(Continued)

*Primary Examiner*—(Jackie) Tan-Uyen T. Ho
(74) *Attorney, Agent, or Firm*—Richard R. Batt

(57) ABSTRACT

Bleeding is controlled on an inner surface of a body cavity by inserting into the cavity an expandable balloon which is covered by a hemostatic shroud, expanding the balloon, and compressing the shroud against the site of bleeding. The balloon may be disposed around a central tube to supply inflation medium. The tip of the device is soft to aid with insertion. The invention includes the corresponding devices and systems for such control of bleeding within a body cavity or passageway, as well as a method of making the devices.

16 Claims, 23 Drawing Sheets

U.S. PATENT DOCUMENTS

| | | |
|---|---|---|
| 5,486,195 A | 1/1996 | Myers et al. |
| 5,514,158 A * | 5/1996 | Kanesaka .................... 606/213 |
| 5,545,176 A | 8/1996 | Murtfeldt |
| 5,645,566 A | 7/1997 | Brenneman et al. |
| 5,827,224 A * | 10/1998 | Shippert ...................... 604/73 |

FOREIGN PATENT DOCUMENTS

| | | |
|---|---|---|
| WO | WO 92/05740 | 4/1992 |
| WO | WO 93/16658 | 9/1993 |
| WO | WO 95/20916 | 8/1995 |
| WO | WO 97/22372 | 6/1997 |

* cited by examiner

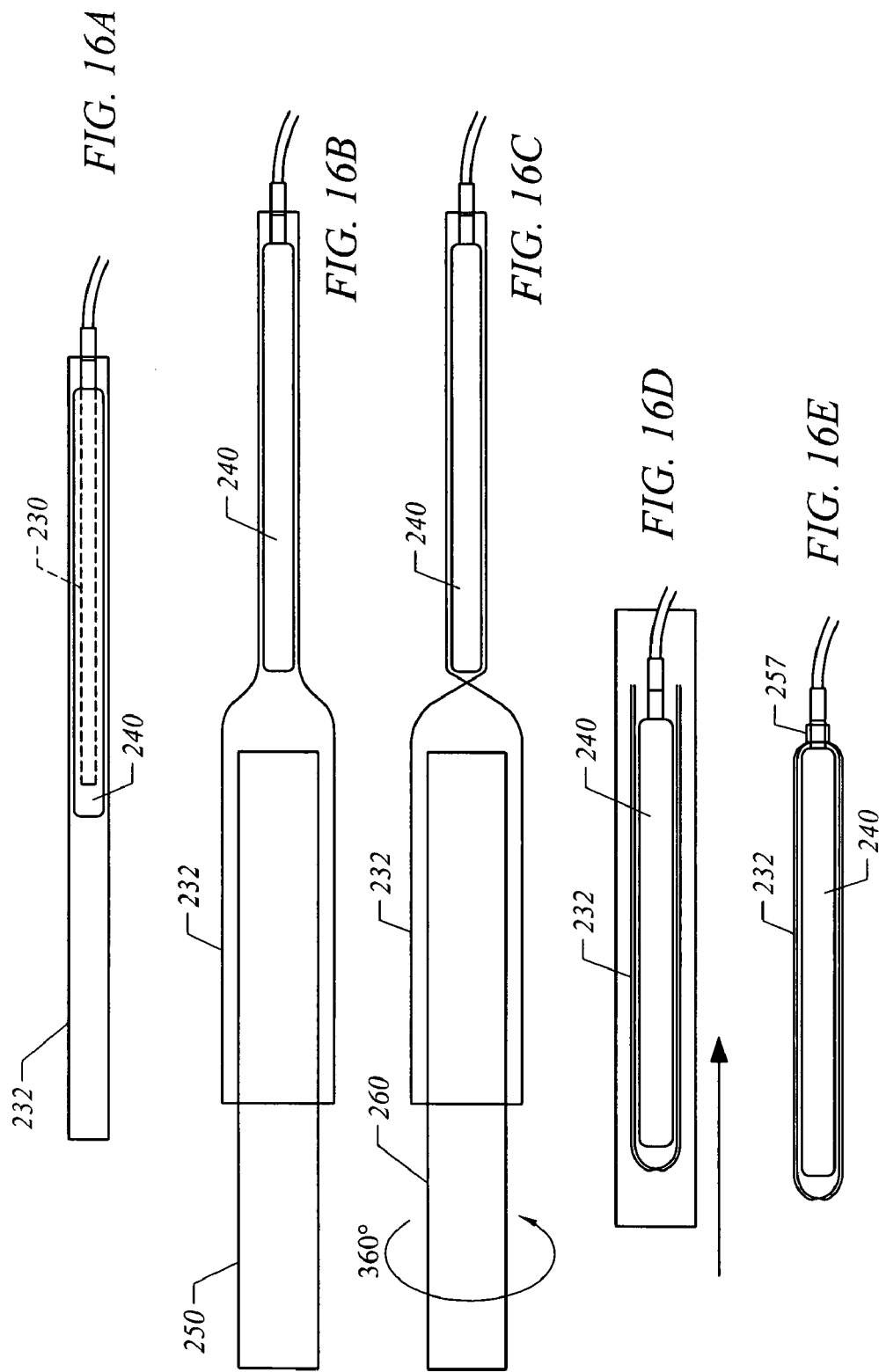

HEMOSTATIC SYSTEM FOR BODY CAVITIES

This application is a continuation-in-part of U.S. patent application Ser. No. 09/927,864 filed Aug. 10, 2001 now U.S. Pat. No. 6,706,051, which in turn is a continuation-in-part of U.S. patent application Ser. No. 09/406,166 filed Sep. 27, 1999 now U.S. Pat. No. 6,306,154, which in turn is a continuation-in-part of U.S. patent application Ser. No. 09/057,414, filed on Apr. 8, 1998 now abandoned.

TECHNICAL FIELD

This invention relates generally to medical devices and methods of use, and more specifically, to materials, apparatus, and methods for facilitating hemostasis within a body cavity or passageway.

BACKGROUND OF THE INVENTION

Nasal passageways, for example, are often susceptible to uncontrolled bleeding caused by various forms of trauma, disease or cellular dysfunction. Methods and devices for controlling, limiting or stopping such bleeding would be useful in a variety of situations, ranging from emergency room care to long term care.

Bleeding is typical after nasal related surgeries or procedures, and epistaxis related to a patient's nasal passageway can be difficult to control. Hemostatic agents, such as carboxymethyl cellulose (CMC) and woven knit or matted fabrics thereof, are known for use in the control of bleeding, such as post-trauma and post-surgical bleeding. CMC is defined as a polycarboxylmethyl ether of cellulose or the sodium salt thereof. It is sometimes referred to as cellulose ether, carboxymethylcellulose, or sodium caramellose. Insertion, application, and subsequent removal of these materials, however, can be difficult in small body passageways, such as nasal cavities.

SUMMARY OF THE INVENTION

The present invention comprises methods and devices for the control of bleeding from an inner wall of a body passageway or cavity. Briefly, the invention comprises an inflatable, expandable balloon, usually covered by a hemostatic shroud, which is inserted into a body cavity, such as a nasal passageway. The shroud is composed of a hemostatic agent; that is, the shroud acts to facilitate or enhance blood clot formation. The balloon component of the present invention is expanded, or inflated, within the cavity in order to press the shroud against the site of bleeding, thereby allowing it to absorb blood and facilitate hemostasis. In specific embodiments, the shroud is composed of a woven or knitted fabric of a hemostatic fiber (such as carboxymethylcellulose) or a reinforced hemostatic fiber. Optionally, this shroud may include an "extension" or "tail" fiber, which upon balloon deflation and removal, facilitates the later removal of the shroud which has been intentionally left in vivo.

The device construction, particularly the balloon construction, may vary according to the particular body cavity. Although a range of different materials can be used for any of the embodiments, there are particular materials which work better than others, depending upon the particular application. For a nasal application, one embodiment includes an inflatable balloon made from a relatively inelastic material.

A particular embodiment of the invention comprises a device for insertion of a shrouded balloon into a nasal passageway by a catheter configured such that the balloon encircles the catheter tube. The lumen of the catheter tube thereby serves as a passageway for breathing. The inflated balloon compresses the shroud against the bleeding nasal wall, thereby facilitating or enhancing hemostasis. The balloon is deflatable such that, upon balloon deflation, the shroud may be left in place on the cavity wall and may be removed at a later time, such as by an attached extension on the shroud.

In another embodiment, there is no central lumen. This gives the catheter a much smaller overall diameter. In patients with small nasal cavities, the lack of the breathing passageway is more than compensated for by the small profile which is far less traumatic and painful during insertion.

The shroud used in the present invention may comprise a woven or knitted fabric combining hemostatic (e.g., carboxymethylcellulose (CMC)) fibers with reinforcing fibers. Alternatively, the shroud may be just a hemostatic agent disposed on the balloon in a film-like covering.

DESCRIPTION OF DRAWINGS

For a better understanding of the present invention, reference may be made to the detailed description which follows, taken in conjunction with the drawings, in which:

FIGS. 16a–16e show the steps for forming a device in accordance with the present invention using a tube tool;

DETAILED DESCRIPTION OF THE INVENTION

The present invention comprises systems, devices, and methods for the control of bleeding in body cavities, such as nasal passageways. Generally, the terms "cavity" and "passageway" may include any bodily cavity, recess, passageway, etc., other than a blood vessel or other component of the vasculature system, and it encompasses those which are healthy and normal as well as those which are abnormal and/or pathological (meaning, diseased or unhealthy).

The term "hemostatic" agent (or material) refers to any agent or material that is capable of arresting, stemming, or preventing bleeding by means other than inducing tissue growth alone. In other words, something other than tissue growth is at least partially responsible for retarding or preventing bleeding. Preferably, the agent or material will be one that enhances blot clot formation. It will, of course, be appreciated that the agent or material may have the beneficial property of inducing tissue growth in addition to retarding or preventing bleeding. Examples of preferred hemostatic agents which enhance blood coagulation include carboxymethylcellulose (CMC), oxidized cellulose, calcium alginate, gelatine, or collagen. CMC can be purchased from Acordis Special Fibres, PO Box 111, 101 Lockhurst Land, Coventry, England, CV6 5RS. Oxidized cellulose such as Tabotamp™, which is sold by Johnson & Johnson, New Brunswick, N.J., U.S.A., is another example of a hemostatic agent. Combinations of different hemostatic agents or materials may be used within the scope of the invention.

The hemostatic agent may be a part of an expansible shroud or may make up the shroud itself. In this later case, the hemostatic agent is either a film or fabric comprised of the hemostatic agent. In the former case, the hemostatic agent is combined with another material, such as a reinforcing fiber material. Typically, the hemostatic agent-containing shroud covers an expansible device such as a balloon. The shroud may be in the form of an expandable tube or in the form of an expandable sheet. In specific embodiments disclosed, the preferred hemostatic agent is a fibrous CMC, which is hemostatic and so will cause blood to clot while at the same time absorbing any exudate. A fabric of CMC fiber is preferred because, aside from its hemostatic properties, it swells and forms a gel, absorbing many times its own weight in fluid when it contacts water (or blood or exudate). Because the CMC material is so hygroscopic, it does not dry into the clotted blood, and therefore can be removed easily without tearing the clot and causing re-bleeding.

Figure 4:
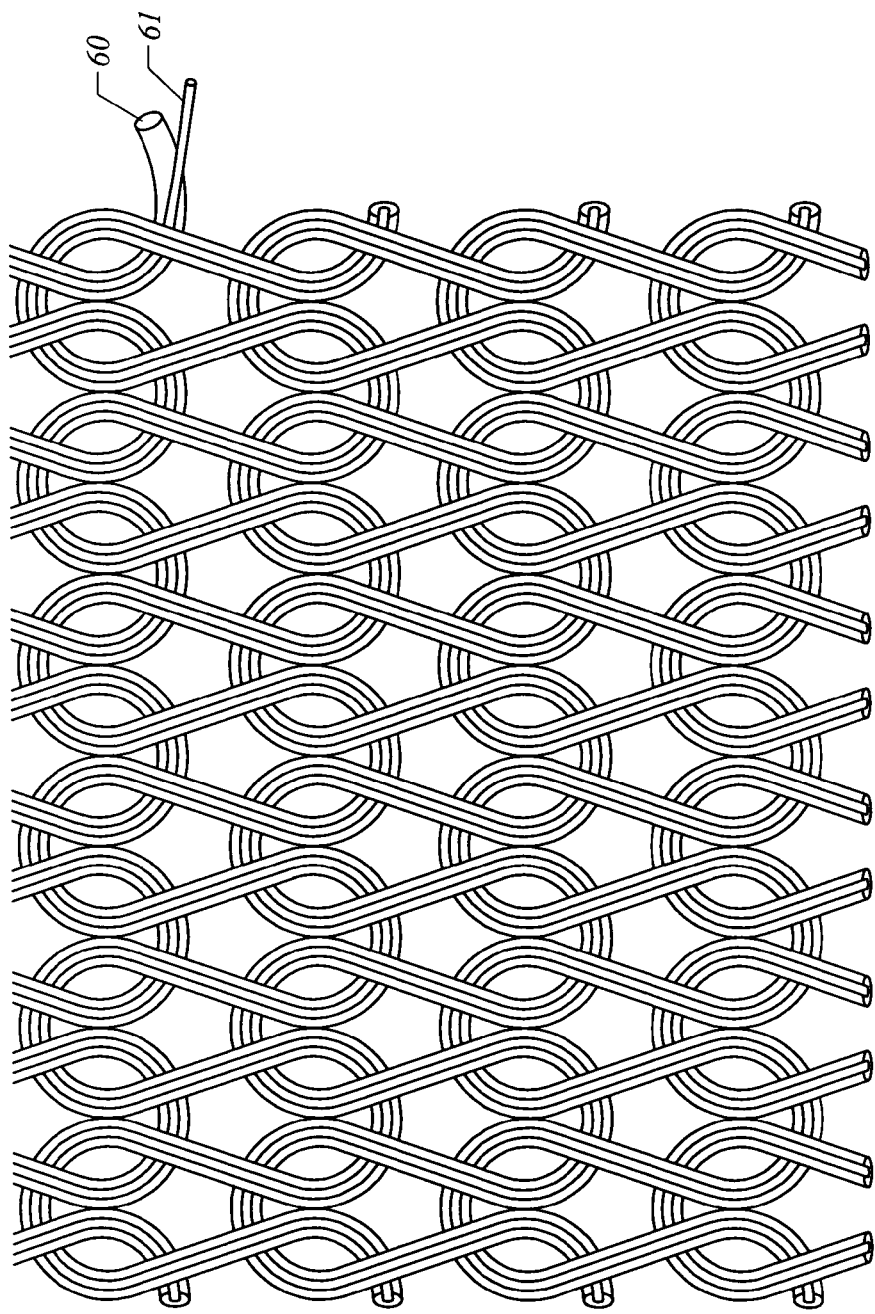
FIG. 4 is a schematic view of a knitted fabric structure useful in the present invention.

Other hemostatic agents which may be used should have absorptive and hemostatic properties similar to those of CMC. In one embodiment, the hemostatic agent fibers are woven or knitted together with reinforcing fibers, such as continuous multifilament polyester or nylon. Such a knitted fabric is illustrated in FIG. 4, and is more fully described and claimed in separate patent applications (U.S. Ser. Nos. 09/406,490 filed Sep. 27, 1999, pending; and 09/612,038 filed Jul. 7, 2000, pending; both of which are incorporated by reference herein). The use of reinforcing fibers provides increased strength to the shroud. This increased strength is important for successful removal of a blood-soaked fabric, where the CMC or gellable material has formed a gel and therefore lost much of its strength.

Examples of some other hemostatic materials include oxidized cellulose, which is conventionally used in knitted form as a hemostatic agent during surgery, and calcium alginate, which is a textile fiber derived from seaweed and is also commonly used as a wound dressing. Furthermore, there are other polysaccharides which are available with similar chemistry and properties to CMC. For purposes of the present invention, the essential properties of the hemostatic material are the ability to absorb large quantities of liquid without becoming enmeshed in the clotted blood. The material must be non-toxic and biocompatible.

Preferably, the shroud is provided in the form of a woven or knitted, especially a weft knitted, textile fabric in which is incorporated the hemostatic material, and which envelops the balloon. The woven or knitted textile material may be permanently or releasably fixed to the balloon.

In some embodiments, particularly those used in nasal applications, the balloon will be made of a relatively inelastic material, such as polyurethane or PVC. Alternatively, for other uses and embodiments, the balloon can be made from an elastomeric material, such as a thin silicone polymer. These balloons can be made by methods known to those skilled in the art, such as by dip molding. As noted above, it is generally desired in nasal applications that the balloon have a fixed volume and be made of an inelastic material. In such a case, the balloon is effectively a bag that can be filled or emptied with an inflation medium. A fixed volume, inflatable, inelastic balloon does not require the inflating medium to first stretch the elastic material of the balloon (as would be the case where the balloon is made from an elastomeric material). All inflation medium pressure is used to fill the cavity. This is essential when the device is used with a pilot balloon to give a tactile feedback of the pressure inside the catheter balloon. With an inelastic, fixed volume balloon, the tactile feedback is truly representative of the pressure applied to the inner surface of the nasal cavity.

For particular non-nasal applications, an elastic material such as silicone rubber can be used for the balloon. Such a balloon may be inflated with a liquid medium such as water or saline solution and the volume controlled by monitoring the volume of fluid inserted. Silicone rubber has the property of being permeable to air but not to water or saline solution.

Figure 1:
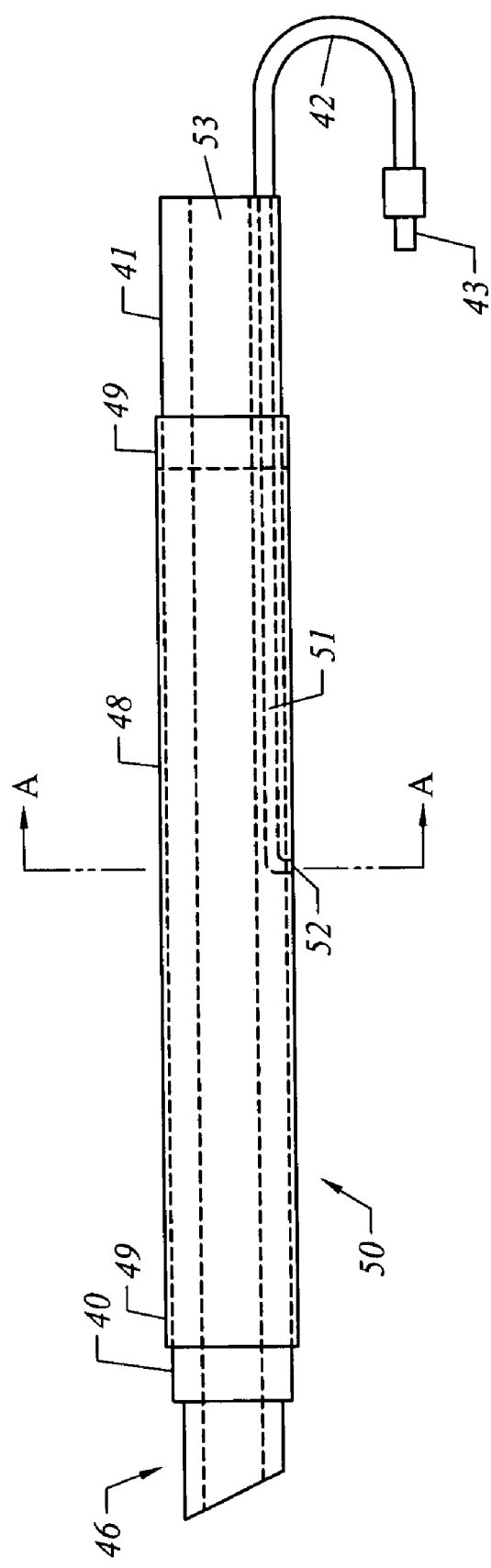
FIG. 1 is a side view of a component adapted for insertion in a nasal passageway.
Figure 2:
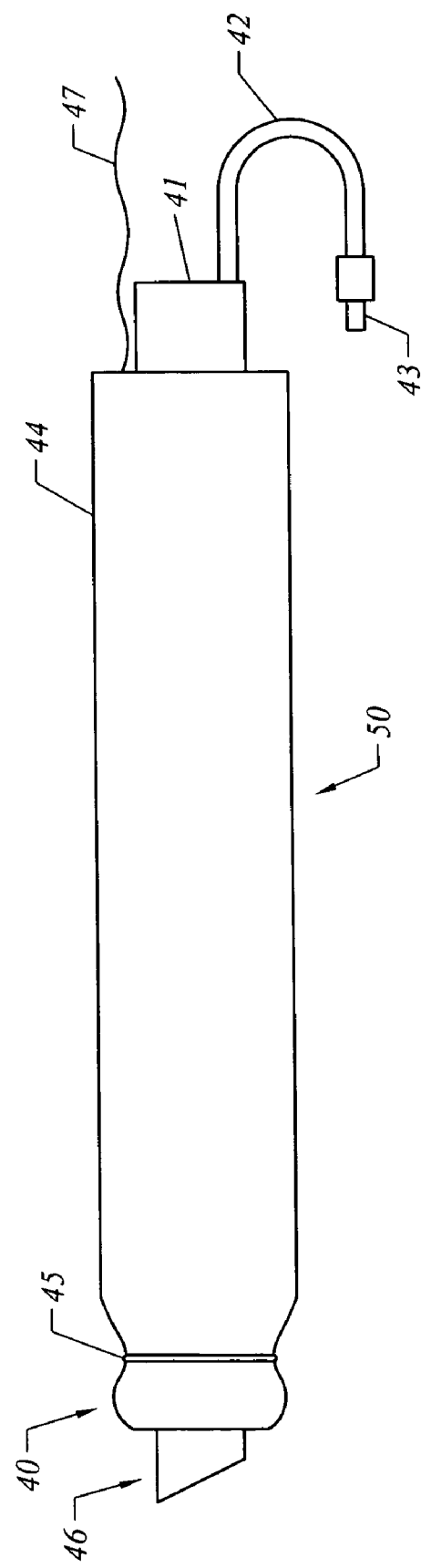
FIG. 2 is a side view of the component shown in FIG. 1 covered with a hemostatic shroud.

One specific embodiment of the present invention which is designed for insertion within a nasal passageway is depicted in FIGS. 1–3. As shown there, a balloon catheter 50 consists of a soft flexible central tube 41, with a long non-elastomeric balloon 48 adhered to the outside wall of central tube 41 along the end sections 49 of balloon 48. The wall of central tube 41 includes an inflation lumen 51 (inflation passageway) which is in communication, through a thin tube 42, with a valve and luer 43 at one end and an inflation port 52 at the other end. The valve 43 is opened by the tip of a standard syringe by which the balloon 48 may be inflated or deflated at will. Tube 41 includes a central breathing lumen 53 which serves as an air passage for breathing.

In a specific exemplary embodiment, central tube 41 has an approximate outside diameter of 10 mm, and an inside diameter of 4–5 mm. The active length is typically between 40 and 100 mm, although shorter or longer lengths may be required for special applications. One end of catheter 46 may have a reduction in the outer diameter in order to provide a shoulder 40. This shoulder is used to locate and maintain the position of an outer hemostatic shroud, (seen in FIG. 2 and discussed in more detail below), during insertion of the device of FIG. 2 into a nasal passageway. In another method of construction the glued neck of the balloon supplies the shoulder and in yet another construction method no shoulder is used and the fabric is retained by a ring and glue or merely by glue alone. Catheter tube 41 typically is comprised of a silicone elastomer or PVC. In the embodiment of the present invention for use in a nasal passageway, the balloon is typically of fixed volume with an expanded diameter of approximately 25 mm and is expanded by inflation with air.

FIG. 2 illustrates the balloon catheter component of FIG. 1 covered by a hemostatic shroud 44 which envelopes a portion of catheter tube 41. Hemostatic shroud 44 can be a soft knitted or woven fabric tube made from a hemostatic material with a high absorption ability. The shroud material is discussed in more detail below. Shroud 44 is draped around the balloon catheter 50 and is positioned by a sewn ring or ligature 45, which locates over shoulder 40 at the distal end 46 of the balloon catheter. The "ring over shoulder" mounting allows shroud 44 to be located precisely over balloon 48 when the device is inserted into the nasal cavity, but permits balloon 48 to be released from shroud 44 by simply withdrawing the catheter. Other methods of locating the shroud may also be used, such as a glued grommet, a welded ring, or by actually shaping the knitted shroud for retention on the balloon. The fabric shroud is highly elastic and deformable which allows it to stretch and/or deform as the balloon is inflated. An extension tail 47 to shroud 44 may be provided as a means to remove the hemostatic element separately after balloon 48 has been removed.

Figure 3A:
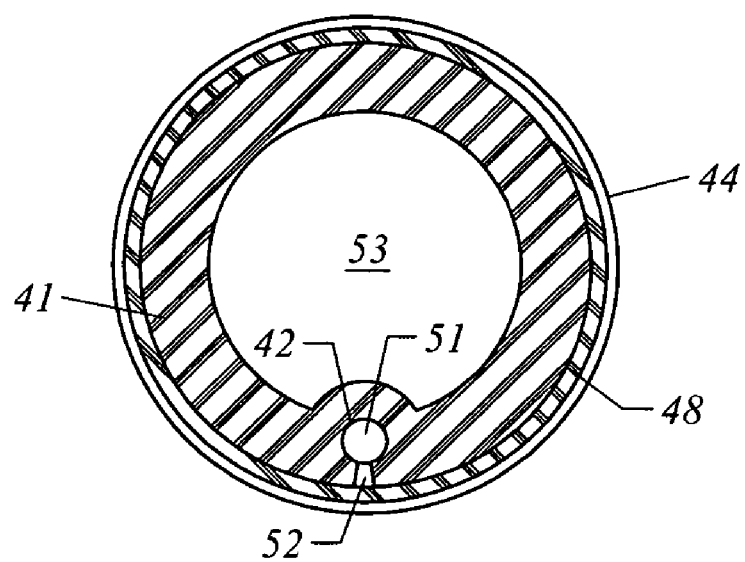
FIG. 3a is a cross-sectional view of a device as shown in FIGS. 1 and 2.

FIG. 3a shows a cross section, in the plane A—A, of nasal catheter 50 of FIG. 1 with hemostatic shroud 44 shown disposed thereon. As shown in FIG. 3, balloon 48 is covered by hemostatic shroud 44, encircling central tube 41 and the non-adhered underside thereof is in communication with inflation port 52.

In service, balloon 48 is inflated by filling material, typically compressed air, from a syringe in communication with valve 43 and the inflation lumen 42 which terminates in port 52 at the inner surface of balloon 48 between the ends of the balloon which are adhered at tube surface areas 49.

FIG. 4 illustrates a schematic view of a preferred fabric for the hemostatic shroud. Specifically, spun CMC yarn 60 is knitted in parallel with a polyester reinforcing yarn 61, as more specifically described in the aforementioned U.S. patent applications incorporated by reference. In this preferred embodiment, the knitted fabric tube is manufactured first by knitting a tube from Lyocell yarn in combination with the reinforcing filament. Lyocell is the generic name for solvent spun cellulose fiber. A brand thereof, "Tencel," (a registered trademark), is available from Accordis Fibres, Coventry UK. Lyocell is produced from the natural cellulose in wood pulp by dissolving the wood pulp in a solvent and then extruding the product through a die called a spinneret. The solvent is then evaporated therefrom, thereby leaving a fiber which is composed of pure cellulose. After knitting, the fabric tube is subjected to a sodium reactant, according to known techniques, which serves to convert the pure cellulose at least partially, into sodium carboxymethylcellulose.

The chemical conversion process is similar to that used to make carboxymethylcellulose sodium USP, except that the raw cellulose is in fiber form rather than the more normal powder form. Other cellulosic raw materials can also be used such as cotton or viscose rayon.

One use of the hemostatic nasal device of FIGS. 1–3 involves inserting into a nasal cavity the shroud-covered balloon catheter 50 illustrated in FIG. 2. Balloon 48 is then inflated. Because the shroud is deformable, it is able to expand and not limit the balloon in its ability to inflate and fill the cavity. The hemostatic fabric is pressed against the vessel wall and into contact with the blood. On contact with blood, the hemostatic shroud, typically CMC (or other similar material) is pressed against the cavity wall and swells to form a gel. It absorbs blood and exudate while its hemostatic properties facilitate and enhance blood clot formation. The lumen of the large (catheter) tube provides for normal breathing, while the inflated balloon provides an anchor for the device. After hemostasis is achieved, the balloon 48 is deflated, and then the catheter is removed. The soft gel nature of the wet fabric shroud ensures that the device does not adhere to the clot. In one embodiment the balloon and tube only are removed and the gelled fabric is left in situ.

Where the gelled fabric alone has been left in situ, the fabric may be removed at any later time by means of the withdrawal string or "tail" 47. Since the hygroscopic nature of the hemostatic fabric prevents the material from sticking to the clotted blood, removal is simple and with minimal chance of restarting the bleeding process.

Figure 3B:
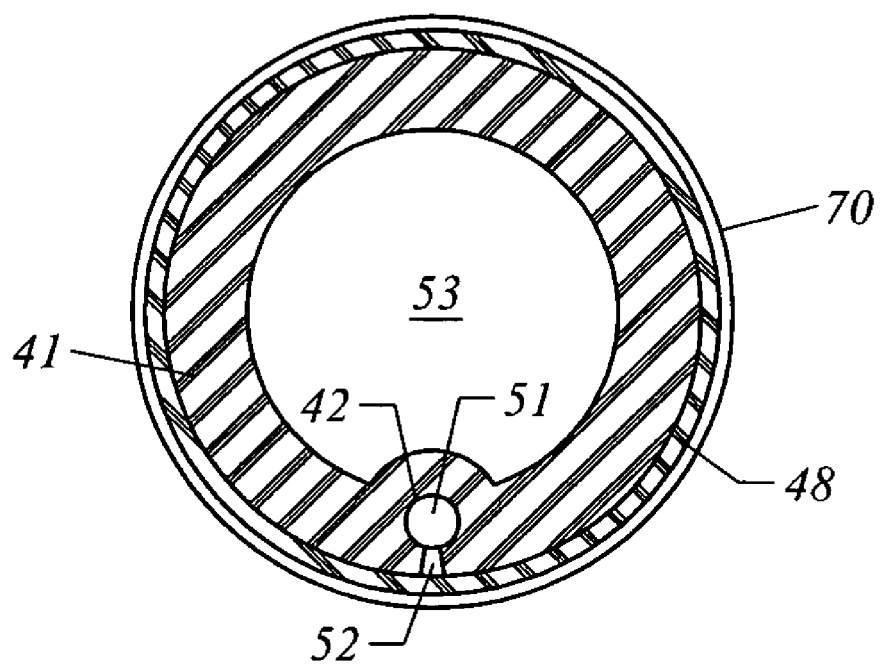
FIG. 3b is a cross-sectional view of a device as shown in FIGS. 1 and 2.

In an alternative embodiment, the outer surface of the balloon itself is coated with an agent that facilitates blood coagulation. In such an embodiment, the shroud does not comprise a fabric of any kind, but is the hemostatic agent itself, provided in the form of a flexible film that coats the outer surface of the balloon. Examples of coating material include gelatin and collagen, but the invention is not limited to these. Such an embodiment is shown in FIG. 3b, which is identical to FIG. 3a except that the shroud 70 is comprised only of a film of hemostatic agent (no fabric). In slight distinction, FIG. 3a shows shroud 44 which is comprised, as described above, of a soft knitted or woven fabric made from a hemostatic material with a high absorption ability.

Pilot Balloon Tactile Pressure Indicator

In another embodiment, the device of this invention may include a tactile pressure-indicating pilot balloon in fluid communication with the balloon by which pressure is exerted on the hemostatic shroud. In such an embodiment, both the shroud compressing balloon and the pilot balloon are expandable. Preferably, both balloons are inflatable but made of a non-stretchable material. In this embodiment, the "balloons" are really more like bags or plastic sacks which receive an inflation medium such as air. Once the balloon is fully inflated, its volume no longer changes because the material of which it is made does not stretch. In use the balloon will typically not be inflated to its maximum volume because the cavity into which the balloon is inflated will preferably be smaller than the theoretical maximum volume of the balloon. This is because the maximum volume and dimensions of the balloon are typically chosen to be larger than the cavity in order that the balloon always has the capacity to fill the cavity. In this way, the hemostatic shroud, which surrounds the balloon, is pressed against the complete inner surface of the cavity.

Figure 5:
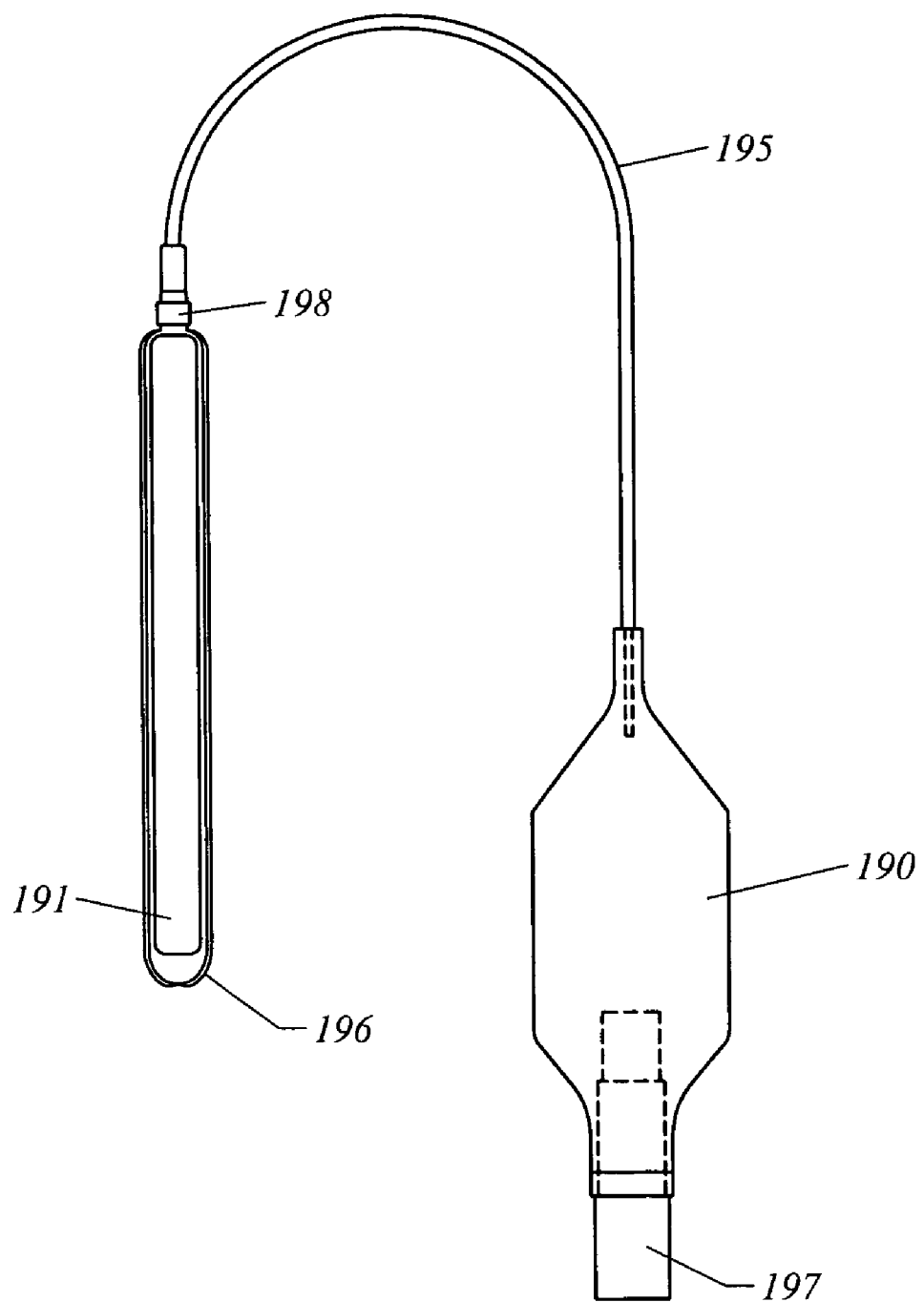
FIG. 5 illustrates another embodiment of the invention which uses a pressure-indicating pilot balloon.

Such a pilot balloon may be disposed at the end of the inflation tube opposite the inflatable balloon of a nasal device as shown in FIG. 5. In this embodiment, pilot balloon 190 is connected to first inflatable balloon 191 via inflation tube 195. Thus, the external tactile pressure sensing pilot balloon 190 does not enter the passageway but allows the user to feel the pressure (usually by grasping the pilot between thumb and finger) within the system as the first inflatable balloon 191 is inflated. In this embodiment, the pilot balloon 190 inflates along with inflatable balloon 190 during placement of hemostatic shroud 196 because the two balloons are in fluid communication with each other. Thus, during placement, the doctor is able to touch the pilot balloon and feel the pressure increase as the system inflates. As discussed above, this may be particularly important in nasal passageway applications, for example, because too little inflation pressure may result in a lack of blood flow stopage, and too great an inflation pressure may damage the passageway. Thus, through a careful tactile determination of system pressure during inflation and placement of the hemostatic fabric, proper and effective use of the device is insured.

In order for the tactile pressure sensing pilot balloon to give a more accurate indication of the pressure inside the nasal cavity, it is preferred that the first inflatable balloon (catheter balloon) be non-stretchable. In accordance with this aspect of the invention, the balloon is made of a relatively inelastic material (such as polyurethane or PVC) in order to have the ability of completely filling a cavity without any energy being used to stretch the wall of the balloon. In such a case, the balloon is effectively a bag that can be filled or emptied with an inflation medium. The inflatable, non-stretchable balloon does not require the inflating medium to first stretch the elastic material of the balloon (as would be the case where the balloon is made from an elastomeric material). This is preferred when the device is used with a pilot balloon to give a tactile feedback of the pressure inside the catheter balloon. With a non-stretchable balloon, the tactile feedback is more representative of the pressure applied to the inner surface of the nasal cavity.

FIG. 5 also illustrates hemostatic shroud 196 disposed on first inflatable balloon 191. As discussed above, various means for introducing air or other suitable pressurizing fluid into the system can be used. FIG. 5 shows a Luer slip valve 197 attached to one end of a pilot balloon 190 the opposite end of which is connected via inflation tube 195. Such slip valves are known to those skilled in the art to provide the introduction of an inflating medium, typically air, into the system. Also shown in FIG. 5 is fabric clamp ring 198 used to hold the hemostatic shroud 196 to the inflation tube and/or base of inflatable balloon 191. In this embodiment, which includes no central tube, inflation tube 195 ends where inflatable balloon 191 and inflation tube 195 connect at clamp ring 198. In the alternative embodiment shown in FIG. 6, an inflation tube 200 actually extends into inflatable balloon 191.

Figure 6:
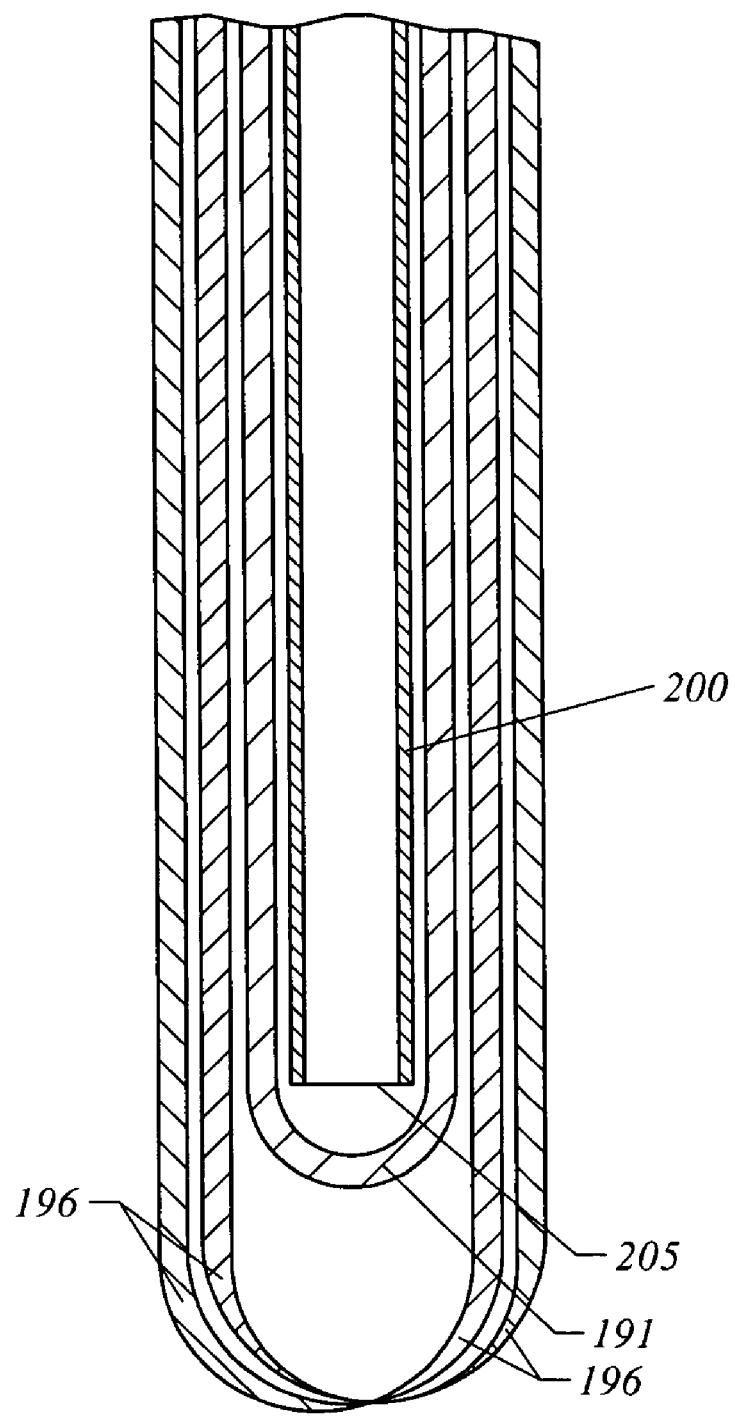
FIG. 6 illustrates a close-up, cross-sectional view of the inflatable balloon and shroud in accordance with the present invention.

FIG. 6 illustrates a close-up, partially cross sectional view of inflation balloon 191 within hemostatic shroud 196. Within inflation balloon 191 is internal inflation tube 200. Internal inflation tube 200 as shown in FIG. 6 is either an integral extension of an inflation tube 195 as seen in FIG. 5, or is a separate piece of tubing in fluid communication with an inflation tube 195 as seen in FIG. 5. Internal inflation tube 200 is shown as open at its end 205 in FIG. 6.

In FIG. 6, the hemostatic shroud 196 is shown folded back over itself along the length of the inflation balloon 191. In assembling the shroud 196 over the balloon 191, half the fabric length is first placed over the balloon and the excess fabric is given a complete turn (or 360° twist) before inverting the twisted excess fabric over the balloon to give the second layer of fabric. This has the effect of closing the fabric over the distal end of the balloon as shown in FIG. 6.

Figure 7:
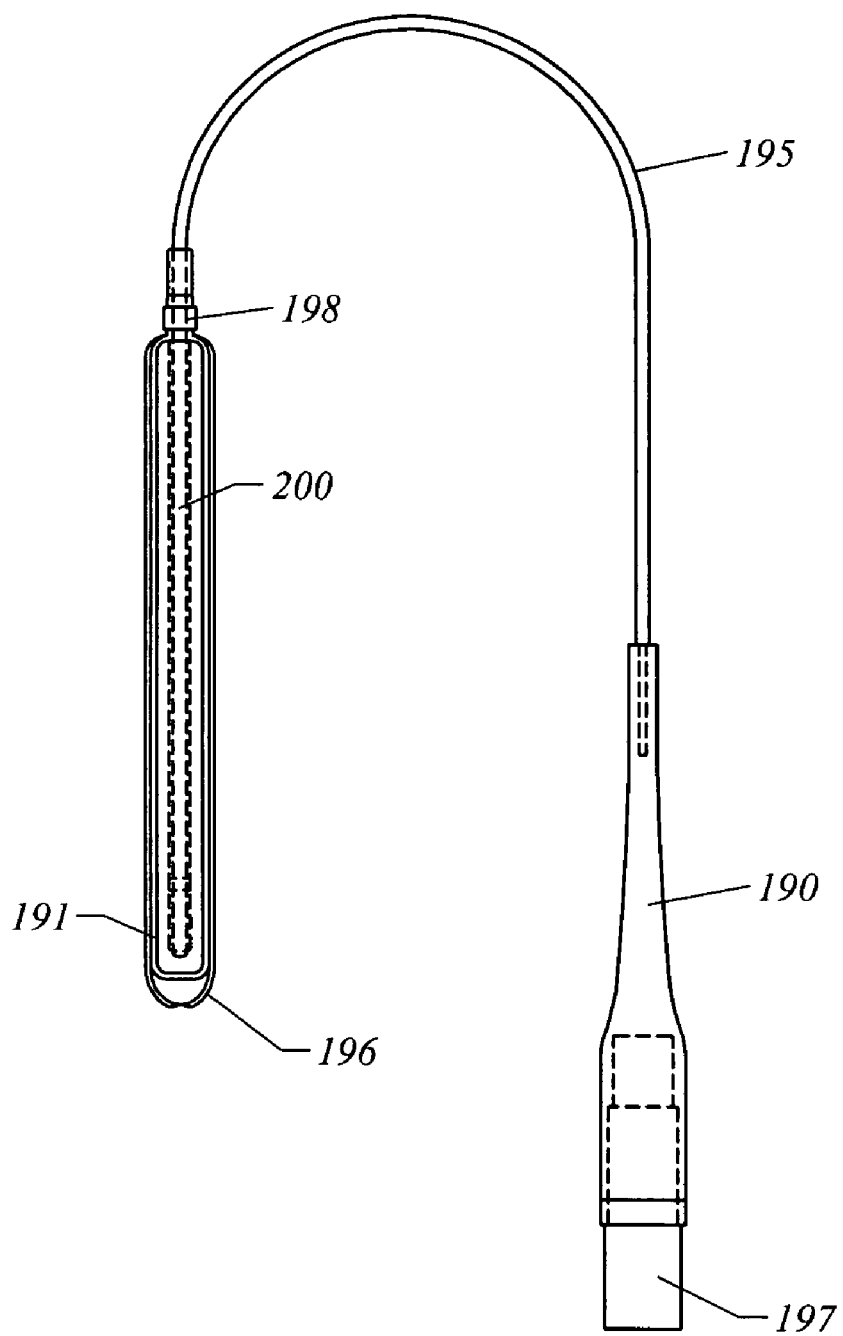
FIG. 7 illustrates the same embodiment as illustrated in FIG. 5 with the pilot balloon deflated and turned 90°.
Figure 8:
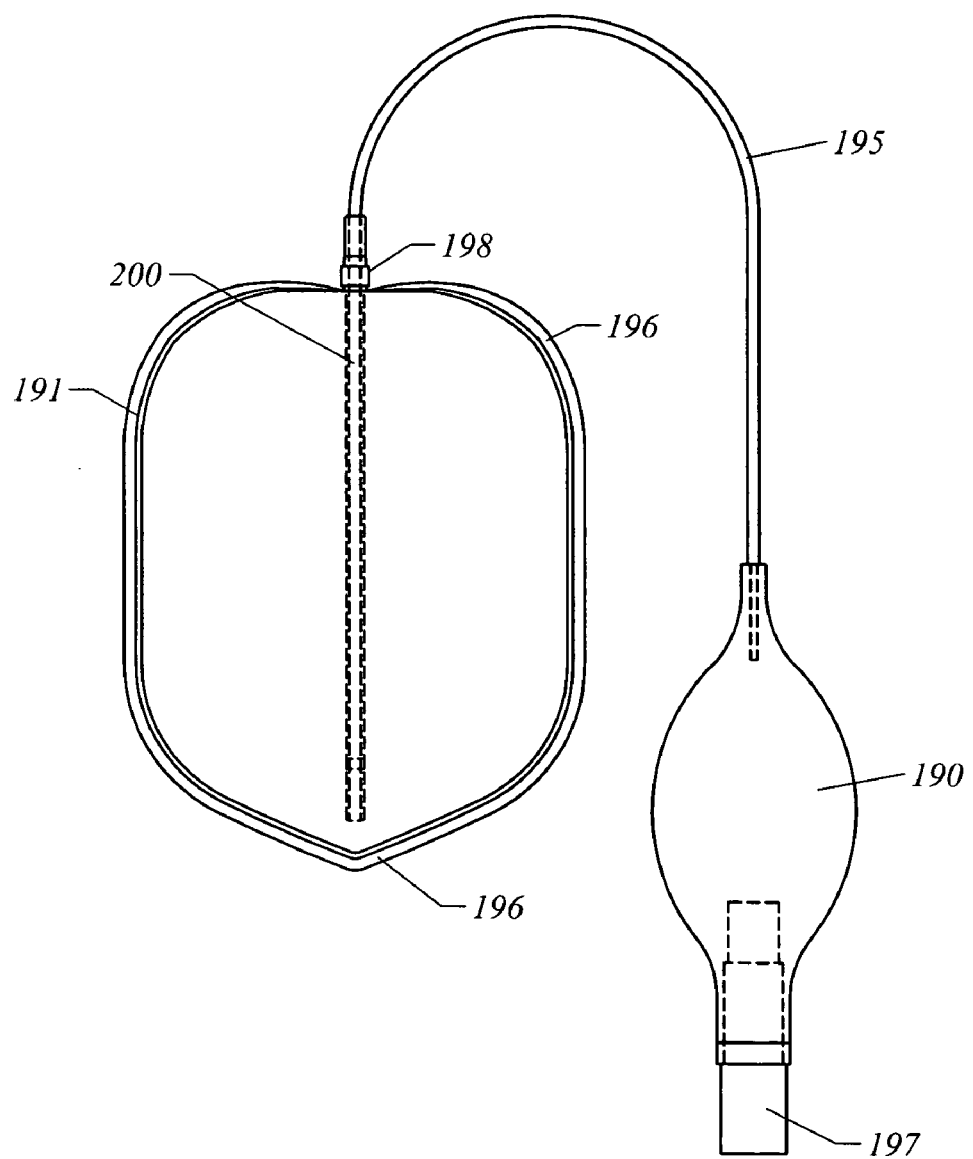
FIG. 8 illustrates the same embodiment as illustrated in FIG. 7 but with the system inflated.

FIG. 7 illustrates the embodiment shown in FIG. 5 with pilot balloon 190 turned 90° from the view shown in FIG. 5. FIG. 6 is presented to illustrate the deflated pilot balloon which accompanies deflated inflatable balloon 191. After an inflation medium (preferably air) is introduced into the system, the resultant configuration of pilot balloon 190 is shown in FIG. 8. This inflated pilot balloon 190, as shown in FIG. 8, when touched or gripped by the doctor using the device, qualitatively indicates the pressure in the system.

In one embodiment, the pilot balloon as illustrated in FIGS. 5–8, has a wall thickness of about 0.09 mm (0.0035 inches) and is comprised of polyvinyl chloride (PVC). Typically, the pilot balloon is approximately 0.5 to 2 inches in length.

In its nasal embodiments, the method comprises the steps of inserting into a nasal cavity a first inflatable balloon surrounded at least in part by a hemostatic shroud comprising a gel-forming absorbent composition. The inflatable balloon is then expanded which compresses the shroud against the inner surface of the cavity where bleeding is to be controlled. Where the device includes a pilot balloon, the pressure inside the inflatable balloon is monitored, during expansion of the inflatable balloon and shroud, by touching the pressure-indicating pilot balloon which is in fluid communication with the first inflatable balloon.

Nasal Applications
  Soft Tip

When it is desired to use the present invention in a narrow body cavity, such as in a nasal application, several embodiments are particularly advantageous. One such embodiment includes a soft tip to allow easier insertion into the nasal cavity as compared to a device not having a soft tip. The soft tip allows for less damage and irritation to the wall of the nasal cavity during insertion, particularly where the cavity does not exhibit smooth or straight walls. For this purpose, a soft tip can be formed on the distal end of a shaft which is configured to be inserted into a particular body cavity.

Figure 9:
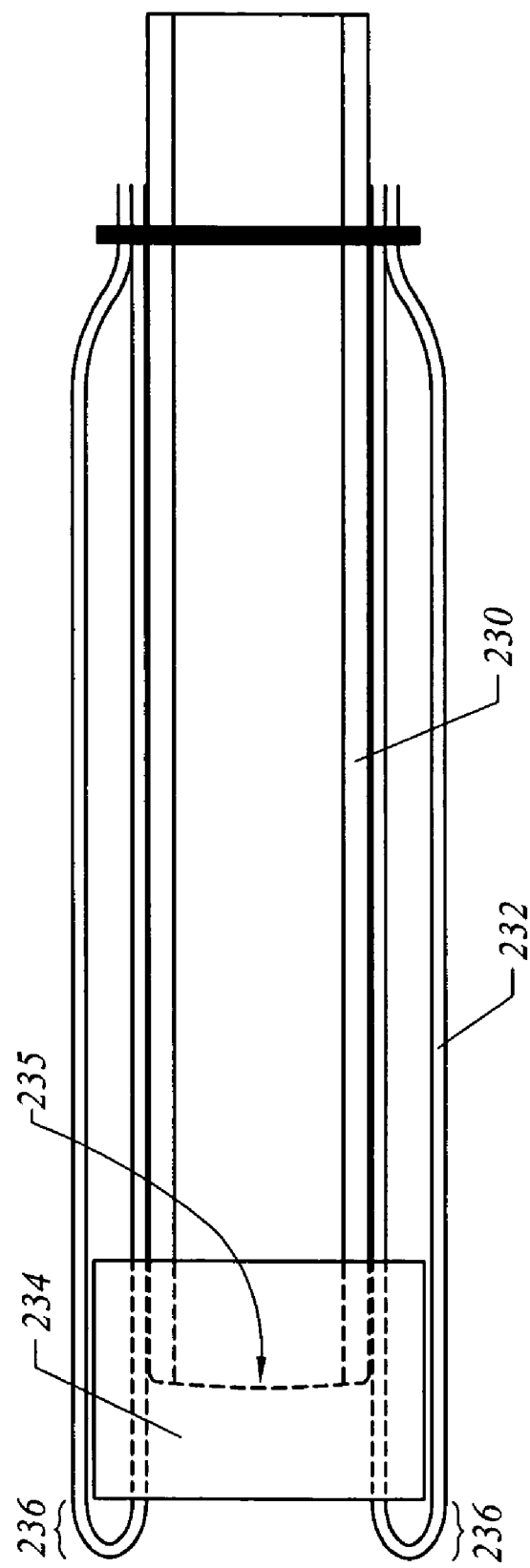
FIG. 9 is a partial cross-sectional view of a device according to one embodiment of the present invention using a clamp ring.

In one such soft-tip embodiment, shown in FIG. 9, central tube 230 is covered along its length by a suitable fabric 232, such as a CMC fabric, or a knitted CMC-reinforcing filament fabric as described above. Fabric clamp ring 234, composed for example of medical grade PVC, is disposed longitudinally on the distal end 235 of central tube 230 and pinches fabric 232 to tube 230. Clamp ring 234 is made from a length of very soft flexible tubing. It is not positioned completely onto tube 230, however, but extends longitudinally beyond distal end 235 of tube 230.

During manufacture of this embodiment, a cylindrical piece of fabric 232 is slipped over central tube 230 and clamp ring 234 is slid over fabric 232 and part way on to central tube 230. Then, fabric 232 is folded back, and inverted, around tube 230 to create a double layer of fabric along tube 230. After fabric 232 is folded, a folded section 236 is created. This folded region 236, draped over the very soft flexible clamp ring 234, forms a soft tip which reduces trauma as the device is inserted into a body passageway.

In one embodiment, glue can be used to set clamp ring 234 into place. The glue would be placed between fabric 232 and tube 230 where the clamp ring overlaps tube 230. A preferred glue is a cyanoacrylate based glue, a more preferred glue being Loctite 4011. Loctite is a registered trademark of Loctite Corporation.

Figure 10:
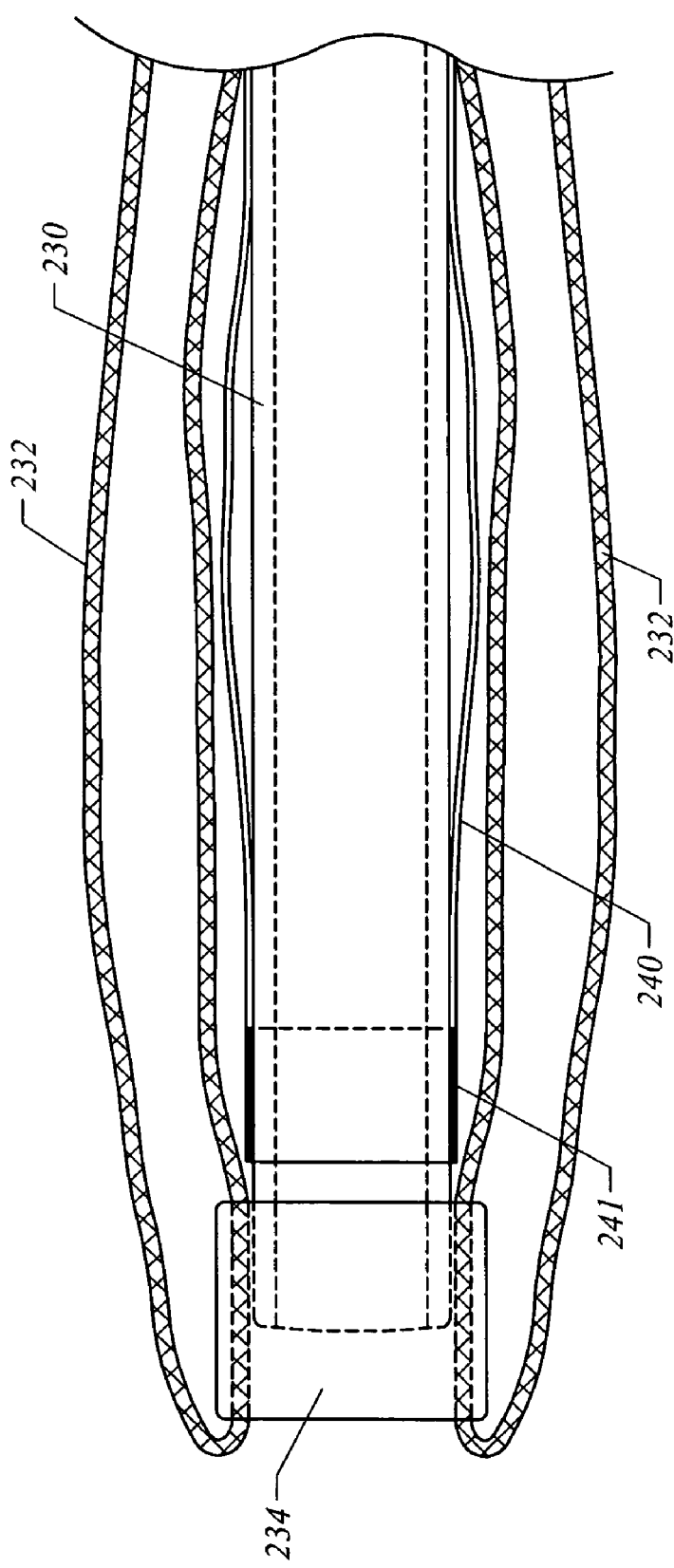
FIG. 10 is a partial cross-sectional view of the device of FIG. 9 having a balloon disposed between the central tube and the shroud.

FIG. 10 shows the embodiment of FIG. 9 but with a balloon 240 disposed between shroud 232 and central tube 230. Balloon 240 is attached toward the distal end of central tube 230 by any of a number of means, including the use of glue or heat sealing the balloon directly to central tube 230 at its distal end 241. Means for inflating balloon 240 are not shown in FIG. 10, but are addressed in other parts of this specification.

Figure 11:
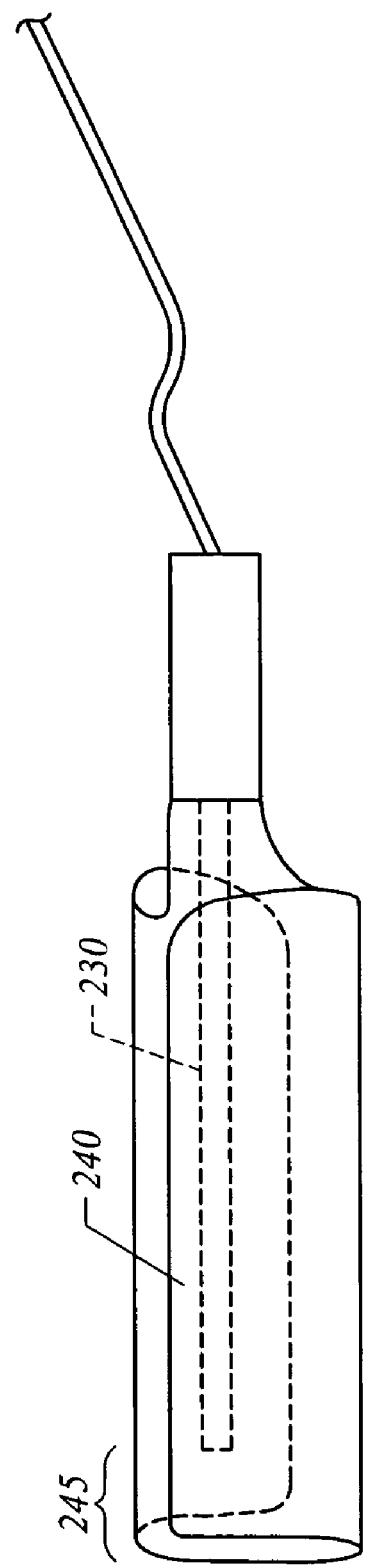
FIG. 11 is a side view of one embodiment of the present invention where the balloon is rolled around a central tube.

A second way to achieve the soft tip of the invention is used on the version which does not include a central airway or breathing tube. This involves rolling the balloon around the central tube or rolling the balloon around itself underneath the fabric (See FIG. 15). In the former embodiment, a thin-walled balloon is disposed on a central tube and, when deflated, is flattened and rolled around the tube around the same longitudinal axis defined by the central tube, similar to how a roll of paper towels are disposed around a cardboard tube. FIG. 11 shows such an embodiment where balloon 240 is rolled around central tube 230. Balloon 240 is sized so as to extend beyond the distal end of central tube 230. The region of extension 245 provides a soft tip for the device which achieves the above described advantages during placement. Preferably, the balloon is made from a film welding technique to achieve a very thin walled balloon. Typical materials for the balloon include PVC and polyurethane. Any suitable polymer would work, so long as it is easily welded and maintains adequate strength to allow expansion of an inflation medium without breaking.

Film welding techniques (including radio frequency welding) are well known to those skilled in the art and are used in a variety of larger products such as blood bags, intravenous (IV) drug bags, pouches for card or badge protection, etc. Generally, the thinner the material, the better, so long as adequate strength is insured. The preferred thickness for the balloon thin film material is between 0.03 mm and 0.15 mm. The combination of this very thin walled balloon along with a thin inflation tube and thin fabric allows for a very small diameter device. The smaller the diameter, the easier the device can be inserted into a nasal passageway.

Figure 12A:
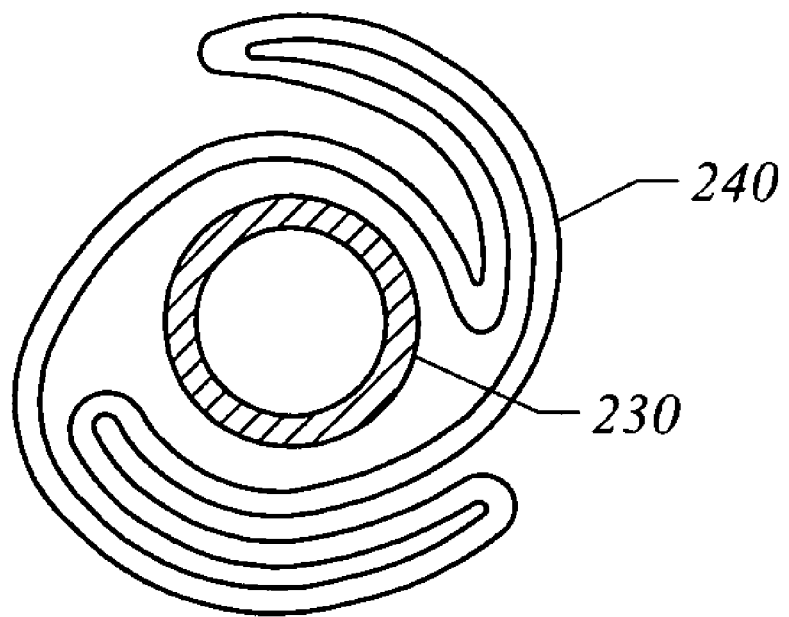
FIG. 12a is a cross-sectional view of the balloon rolled around the central tube.
Figure 12B:
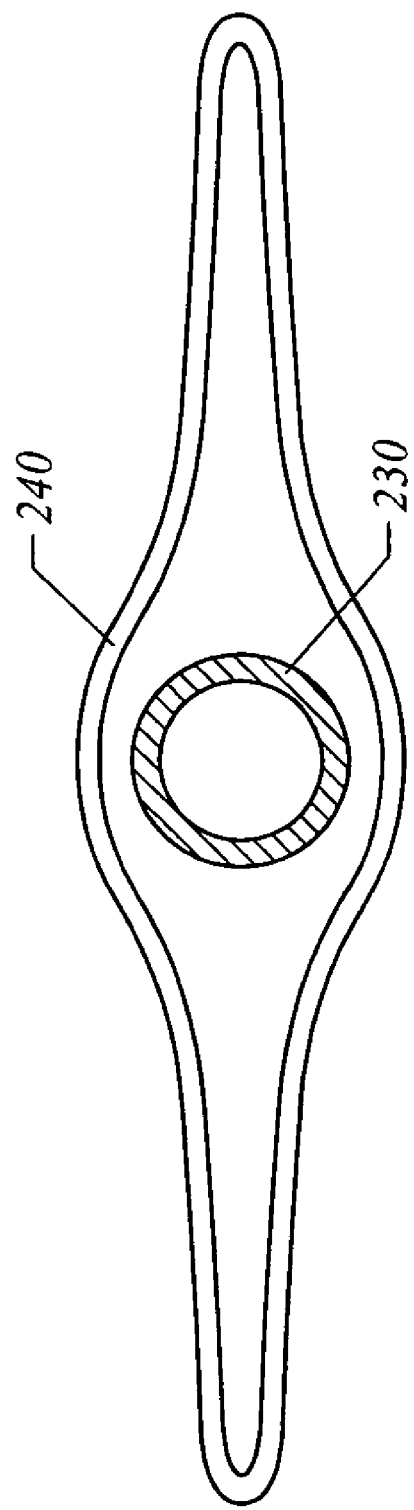
FIG. 12b is a cross-sectional view of the balloon unrolled and deflated around the central tube.
Figure 12C:
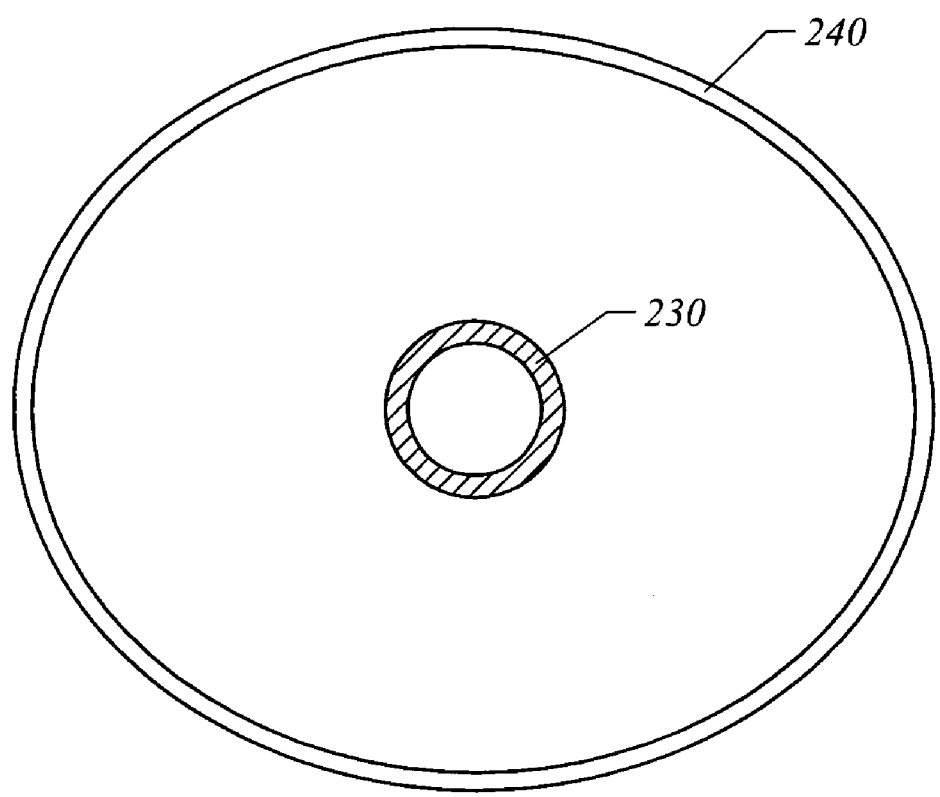
FIG. 12c is a cross-sectional view of the balloon inflated around the central tube.
Figure 13:
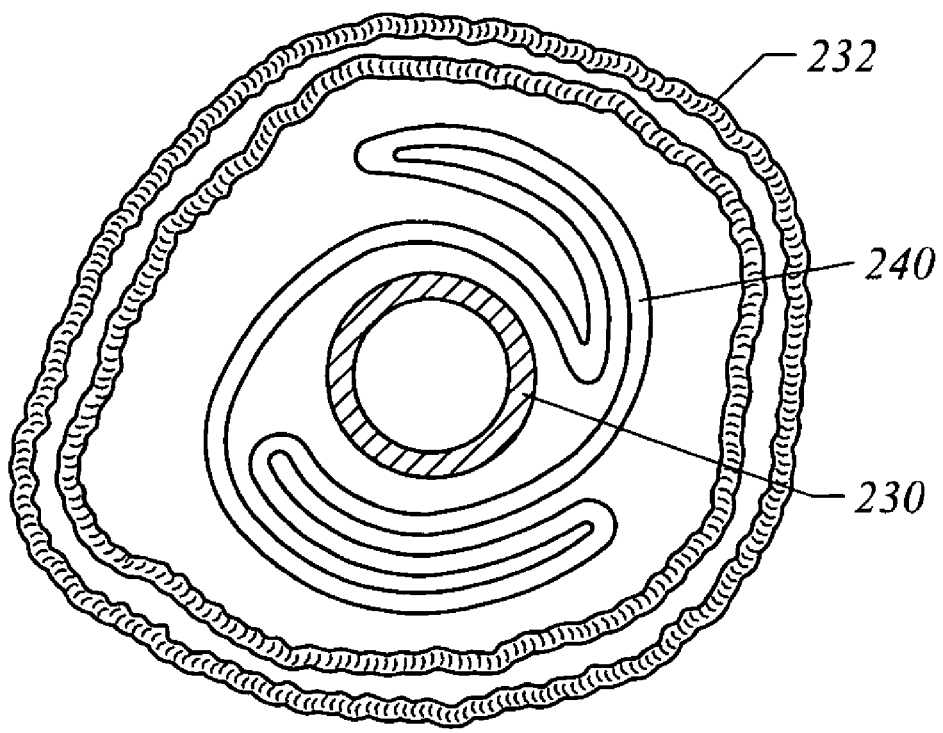
FIG. 13 is a cross-sectional view of the balloon rolled around the central tube, with a shroud disposed therearound in accordance with the present invention.
Figure 14:
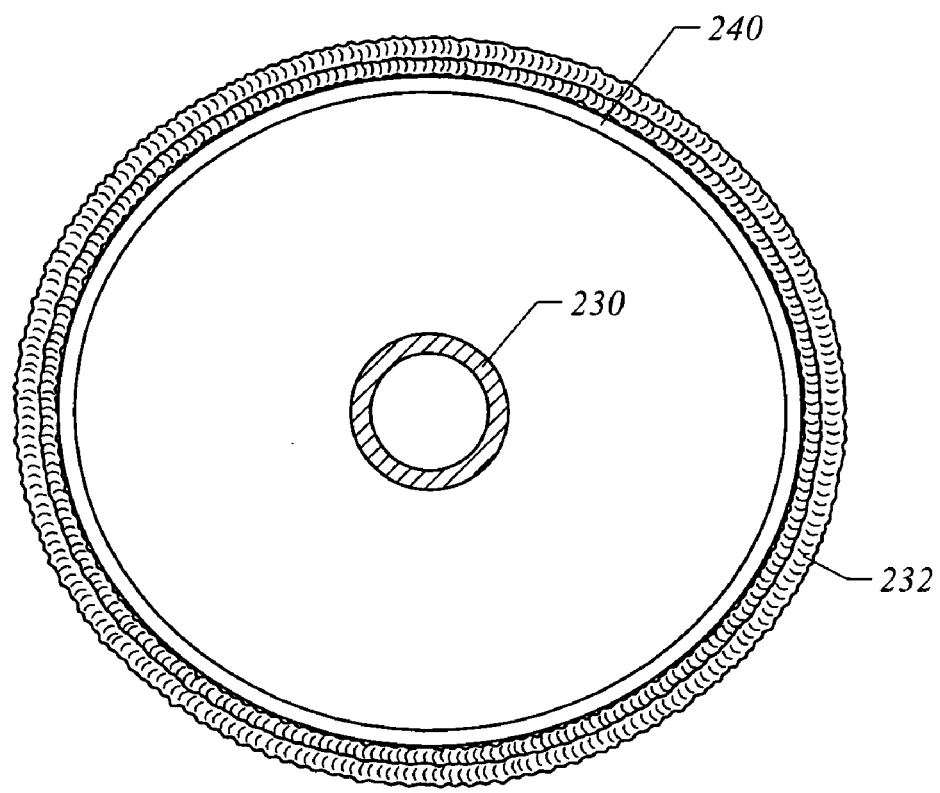
FIG. 14 is the cross-sectional view of FIG. 13 but with the system inflated.

FIGS. 12a–12c show three cross sections of balloon 240 and central tube 230. FIG. 12a shows the balloon rolled around central tube 230. FIG. 12b shows the balloon 240 unrolled but not fully inflated around central tube 230, and FIG. 12c shows the balloon 240 inflated around central tube 230. FIG. 13 shows the cross section of FIG. 12a with shroud 232 shown disposed around the balloon 240. When central tube 230 receives inflation medium (typically air), the medium passes through a passageway, typically a hole (not shown) in the wall of tube 230 and into the interior of balloon 240. Balloon 240 then expands and unrolls within shroud 232 and expands to cause shroud 232 to contact the inner surface of the body passageway or cavity where bleeding is to be controlled. FIG. 14 shows balloon 240 expanded within shroud 232. FIGS. 13 and 14 show the shroud 232 as a two layer shroud, consistent with the embodiment shown in FIG. 10. The shroud could, however, be single layered or have more than two layers.

Figure 15:
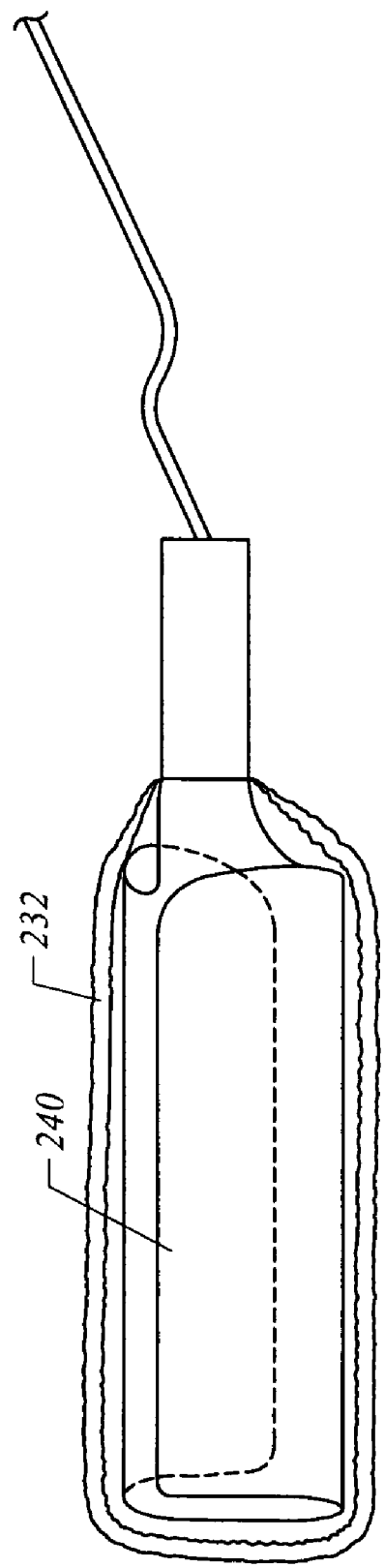
FIG. 15 is a side-view of the device shown in FIG. 11 but without the central tube.

The balloon rolling does not have to be rolled around a central tube. As described above, no central tube is present in some embodiments. In such a case, the fabric would be disposed around a rolled balloon where the balloon is simply rolled up on itself. An example of this later embodiment is shown in FIG. 15. A tubular connection for introducing inflation media would obviously be included. A forceps or other instrument may be required to deploy such an embodiment.

Twisted Fabric Construction

In another embodiment, the shroud is attached to the inflation lumen at only the proximal end of the device, as shown in FIGS. 6 and 16e. Here, shroud 232 is doubled-up, back over itself along the length of central tube 230. In this embodiment, however, and unlike the embodiment shown in FIG. 9, the assembly of shroud 232 over balloon 240 involves the twisting of the fabric at its distal end. Here, half the fabric length is first placed over the balloon and the excess fabric is turned, preferably in a complete turn (or 360° twist) at its distal end before inverting the twisted excess shroud back over the balloon and first layer of shroud to provide the second layer of shroud. This has the effect of closing the shroud over the distal end of the balloon as shown in FIG. 6. In such an embodiment, balloon 240 is only secured to central tube 230 at its proximal end. This allows for the use of only one attachment means for the entire device, such as glue or a clamp ring 257.

The present invention also includes a method for manufacture of a device as represented in FIG. 6. This method, as shown in FIGS. 16a–16e, involves the use of an assembly tool 260 as shown in FIG. 16b. This tool is a relatively thin-walled cylinder and is made from a relatively rigid, or stiff, preferably transparent material.

The method first requires the placement of shroud 232 over the balloon 240 and central tube 230, as shown in FIG. 16a. In the next step, assembly tool 260 is pushed into shroud 232, which shroud is simultaneously stretched around the outside surface of assembly tool 260, as shown schematically in FIG. 16b. FIG. 16c illustrates the third step, which requires rotating assembly tool 260, and shroud 232 along with it. The preferred rotation is 360°, although more rotation would achieve the same purpose. The next step is shown in FIG. 16d, which illustrates the progression of assembly tool 260 toward the proximal end of the device, which causes shroud 232 to double over on itself, forming a double layer of fabric along the outside surface of balloon 240. FIG. 16e shows the result of this method, after a clamp ring 257 is placed around shroud 232 at the proximal end of the device, thereby securing the fabric in place. Any excess fabric that would extend beyond the clamp ring 257 could then be trimmed from the device.

Glue could also be used with this embodiment. During the step of placing clamp ring 257, a small amount of glue could be injected under the clamp ring at two spots, one each at 180° from the other around the circumference of the inflation tube where clamp ring 257 will be secured. Because the fabric is meshed, in the preferred embodiment, the glue will contact the fabric, the inflation tube, and the inside of the clamp ring, binding all three components together.

This method can also be used to place fabric around a device which has no central inflation lumen, but which has only an inflation balloon attached to the distal end of the inflation tube. Such an embodiment is shown in FIG. 5. In such a case, only the balloon and fabric extend beyond the distal end of the inflation tube.

Figure 18:
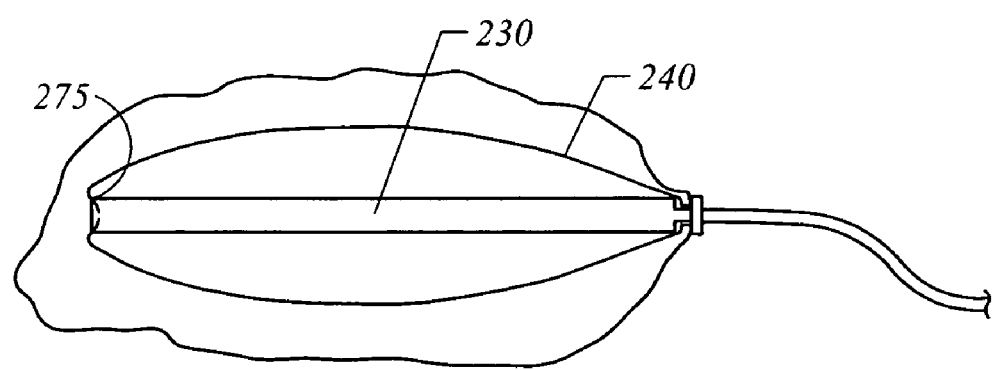
FIG. 18 shows a side, partial cross-sectional view of a central tube without a deflation hole during deflation.

In some embodiments of the invention, particularly those not including a breathing lumen, there is a risk that upon deflation, the balloon and/or surrounding fabric will be sucked into the passageway by which inflation medium passes from the central tube into the balloon. This is illustrated in FIG. 18, wherein balloon 240 is shown sucked into a blocking position at distal end 275 of central tube 230. This may result in preventing complete deflation of balloon 240.

Figure 17A:
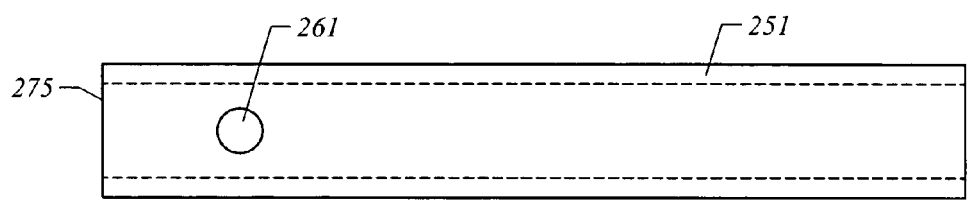
FIGS. 17a and 17b show a deflation hole in a central tube in accordance with one embodiment of the present invention.
Figure 17B:
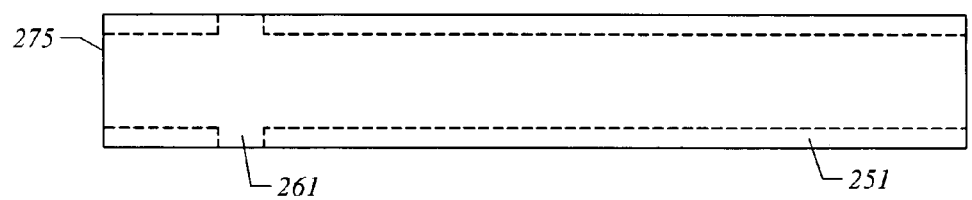
Figure 19:
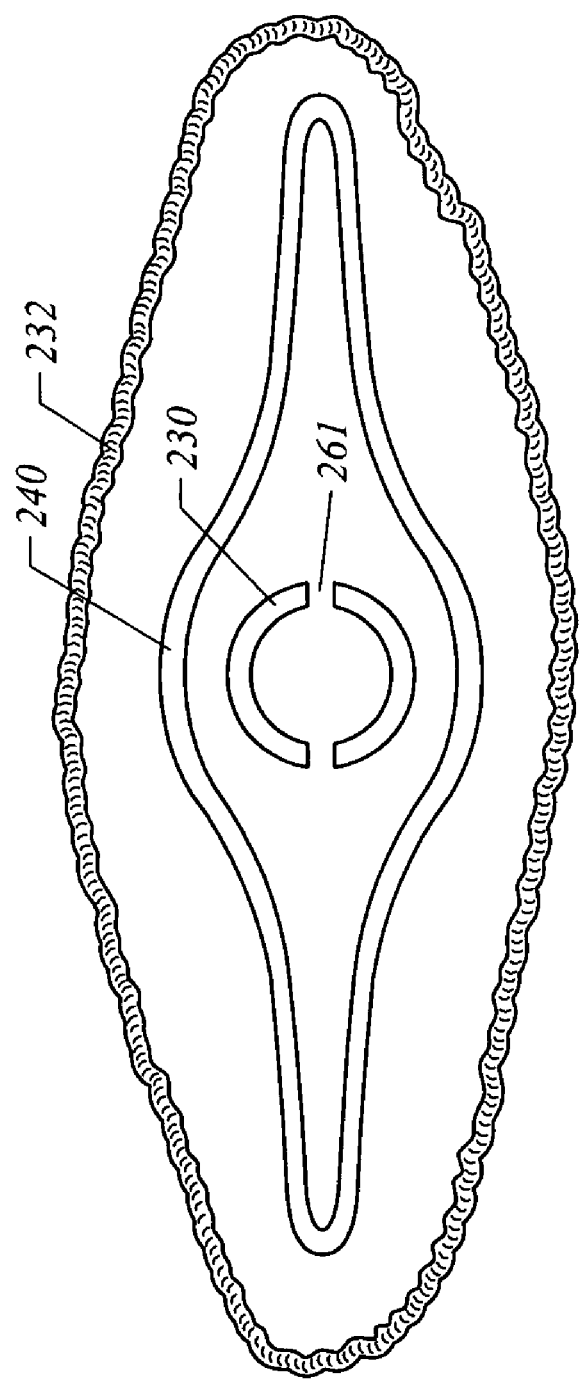
FIG. 19 is a cross-sectional view of the device with an inflation/deflation hole.

To prevent this potential problem, a hole may be formed in the central tube wall as shown in FIGS. 17a, 17b, and 19.

As shown in FIGS. 17a and 17b, hole 261 is formed so that inflation medium can enter and be withdrawn from a balloon surrounding the central tube 230. The inflation medium can pass both at the distal end of the central tube 230 and laterally through hole 261. This prevents a deflation limitation or stopage which could result at the distal end of central tube 230, as shown in FIG. 18. FIG. 19 shows a cross-sectional view of central tube 230 having hole 261 with balloon 240 and shroud 232 disposed therearound.

Figure 20:
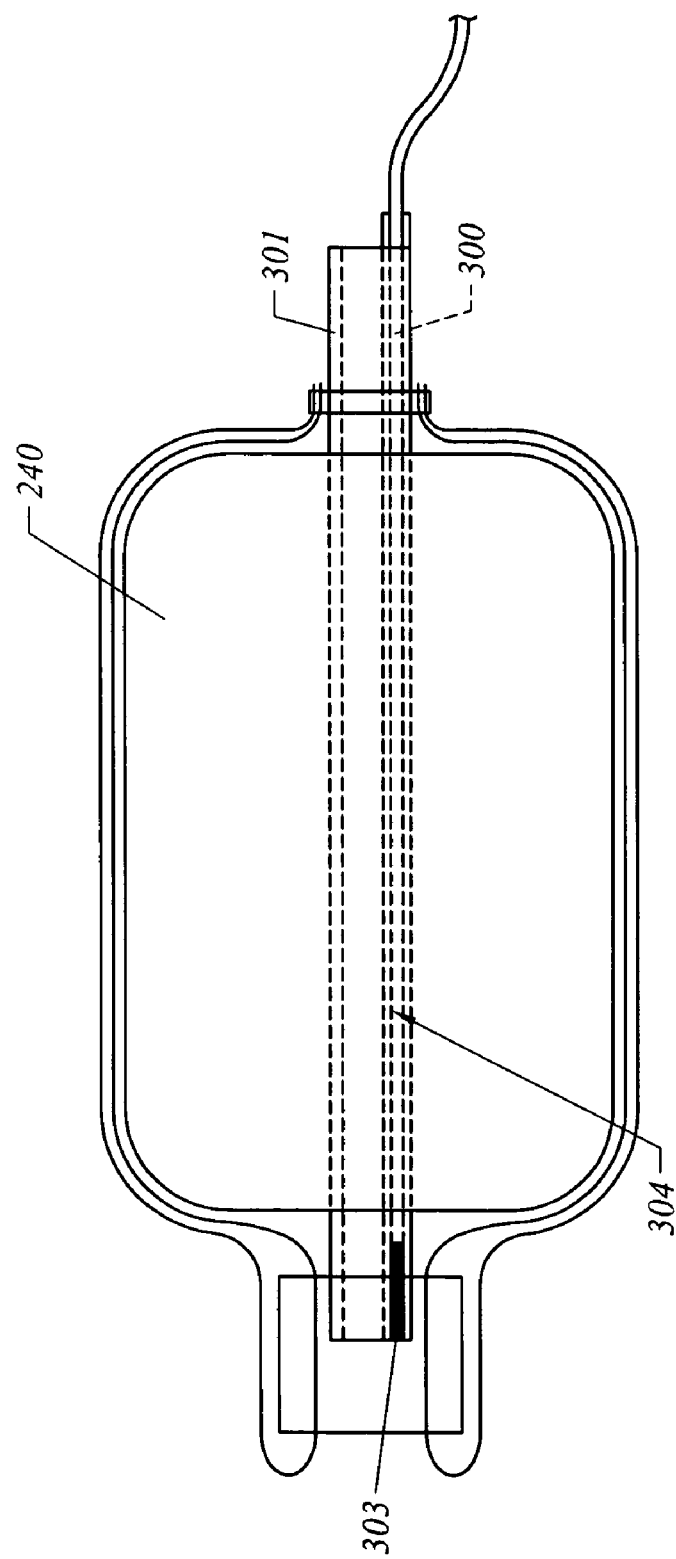
FIG. 20 shows a device in accordance with the present invention where the inflation tube is not coaxial with a breathing lumen, and the inflation tube has an inflation/deflation hole.

FIG. 20 illustrates an embodiment having a breathing tube 301 where inflation lumen 300 is disposed within the wall of breathing tube 301. In this embodiment, balloon 302 is shown disposed around breathing tube 301, and inflation lumen 300 is disposed radially offset from the central axis of breathing tube 301. Here, inflation lumen 300 extends along the entire length of breathing tube 301, and is blocked at its distal end by glue 303. Alternatively, inflation lumen 300 could be formed so as not to continue all the way to the end of the breathing tube 301 (as shown in FIG. 1). The important aspect of inflation lumen 300 is that it not be open at the breathing tube's distal end.

To allow delivery of inflation medium to balloon 302, a hole 304 is provided along inflation lumen 300. The hole could be formed from a number of different techniques. A preferred method of making the hole in this embodiment includes the use of a punch. The punch is a metal tube, with one end sharpened like a circular knife, which is inserted into the side of breathing tube 301 only far enough to create the hole 304. The use of a punch, instead of a conventionally drilled hole, helps insure that a conventional drill does not continue into the breathing passageway and open a hole there during manufacture of the device.

An additional advantage to using the punch, instead of a conventional drill, is that, unlike a conventional drill, the punch cuts a clean hole and does not create loose material or shavings which could be difficult to remove from the device and could cause a contamination hazard during later use of the device. By using the punch, the punched material is removed within the shaft of the punch and discarded.

The foregoing comprises a description of certain exemplary embodiments of the present invention. The invention is not limited to these embodiments, however, and the subjoined claims are intended to be construed to encompass all embodiments of this invention, and equivalents and variants thereof, which may be made by those skilled in the art without departing from the true spirit and scope of the essential concepts disclosed and claimed herein.

What is claimed is:

1. A device for controlling bleeding on an inner wall of a body cavity or passageway comprising:
    an insertable shaft having a distal end, said shaft comprised of a hemostatic shroud disposed around an inner component, said inner component having a distal end, said shaft having a soft tip on said distal end of said shaft,
    and said shroud disposed around said shaft and extending beyond both the distal end of said inner component and the distal end of said shaft.

2. The device of claim 1, wherein said inner component comprises a central tube and said soft tip comprises a length of said hemostatic shroud, supported by a length of soft flexible tubing projecting beyond the distal end of said central tube.

3. The device of claim 1, wherein said inner component comprises a balloon and said soft tip comprises the distal end of said balloon covered by said hemostatic shroud.

4. The device of claim 3, wherein said inner component comprises a central tube and said balloon is rolled around said central tube, the distal end of said balloon extending beyond the distal end of said central tube.

5. The device of claim 4, wherein said inner component is a balloon and does not include a central tube.

6. The device of claim 3 wherein said balloon is inelastic.

7. The device of claim 2 wherein a first portion of said hemostatic shroud surrounds said inner component and a second portion thereof extends beyond the distal end of said inner component and is folded back over the first portion.

8. The device of claim 1 wherein said hemostatic shroud is comprised of a fabric comprised of a gel-forming absorbent composition.

9. The device of claim 1 wherein said hemostatic shroud is comprised of a gel-forming absorbent composition film.

10. The device of claim 1 wherein said hemostatic shroud is comprised of hemostatic agent fibers knitted or woven together with reinforcing fibers.

11. The device of claim 10 wherein said reinforcing fibers are one of polyester and nylon.

12. The device of claim 1 wherein said hemostatic shroud is comprised of hemostatic agent yarn knitted or woven together with reinforcing yarn.

13. The device of claim 12 wherein said reinforcing yarn is comprised of nylon or polyester.

14. A device for controlling bleeding on an inner wall of a body cavity or passageway comprising:
    an insertable shaft having a distal end, said shaft comprised of a hemostatic shroud disposed around an inner component, said inner component having a distal end and a balloon, said shaft having a soft tip on said distal end of said shaft,
    and said shroud disposed around said shaft and extending beyond both the distal end of said inner component and the distal end of said shaft.

15. The device of claim 14, said soft tip comprises the distal end of said balloon covered by said hemostatic shroud.

16. The device of claim 14 wherein said balloon is inelastic.

* * * * *